United States Patent
Brennen et al.

(10) Patent No.: US 8,647,590 B2
(45) Date of Patent: Feb. 11, 2014

(54) OPTICAL DETECTION CELL WITH MICRO-FLUIDIC CHIP

(75) Inventors: Reid A. Brennen, San Francisco, CA (US); Timothy Beerling, San Francisco, CA (US); Hongfeng Yin, Cupertino, CA (US); Kevin P. Killeen, Woodside, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1692 days.

(21) Appl. No.: 11/384,149

(22) Filed: Mar. 16, 2006

(65) Prior Publication Data
US 2007/0217953 A1    Sep. 20, 2007

(51) Int. Cl.
G01N 21/00    (2006.01)

(52) U.S. Cl.
USPC ............... 422/503; 422/82.05; 422/82.08; 422/82.09

(58) Field of Classification Search
USPC ............... 422/401, 402, 502, 503, 68.01, 422/82.05–82.09
See application file for complete search history.

(56) References Cited

U.S. PATENT DOCUMENTS

| | | | |
|---|---|---|---|
| 4,040,083 A | 8/1977 | Saiki et al. | |
| 5,658,413 A | 8/1997 | Kaltenbach et al. | |
| 5,757,482 A | 5/1998 | Fuchs et al. | |
| 6,526,188 B2 | 2/2003 | Dourdeville et al. | |
| 6,605,472 B1* | 8/2003 | Skinner et al. | 436/171 |
| 6,671,300 B2 | 12/2003 | Marsh et al. | |
| 2002/0113009 A1* | 8/2002 | O'Connor et al. | 210/511 |
| 2002/0180963 A1* | 12/2002 | Chien et al. | 356/246 |
| 2003/0032048 A1* | 2/2003 | Kim et al. | 435/6 |
| 2004/0089057 A1 | 5/2004 | Hobbs et al. | |
| 2005/0257885 A1 | 11/2005 | Hobbs | |

OTHER PUBLICATIONS

Union Optic [online] retrieved from http://www.u-optic.com/material.htm.
Office Action mailed Nov. 27, 2009 in co-pending U.S. Appl. No. 11/384,149.
Office Action mailed Jul. 6, 2013 in co-pending U.S. Appl. No. 11/384,149.
Brewster, "Thermal Radiative Transfer and Properties", John Wiley & Sons, Inc., 1992, Front matter & p. 165.
Pavon, et al. "Universal sandwich membrane cell and detector for optical flow injection analysis", Analytical Chemistry vol. 64. No. 8, Apr. 15, 1992, p. 923-929.

* cited by examiner

Primary Examiner — Paul Hyun

(57) ABSTRACT

The present invention relates to an optical detection cell for micro-fluidics. The detection cell provides a first layer, a detection cell layer contacting the first layer, a third layer contacting the detection cell layer, a micro-fluidic chip having a fluidic port and a detection channel defined through the detection cell and being in fluid communication with the fluidic port of the chip, the detection channel serving as a light path for receiving light for detecting a molecule. Methods of detecting molecules and making the detection cell are also disclosed.

9 Claims, 3 Drawing Sheets

OPTICAL DETECTION CELL WITH MICRO-FLUIDIC CHIP

BACKGROUND

Various detection devices and detection cells have been designed for identifying and characterizing small molecules. Typical devices may include, UV VIS, fluorimeters or micro-fluidic devices. Most of these devices provide some type of detection cell with limited volume for holding the sample while light is passed through the cell. This allows for conservation of sample and increase of signal to noise (i.e. improve characterization and detection).

Most of these devices and cells operate by first placing a buffer or a fluid medium in the detection cell. Then light of a defined wavelength is passed through the medium and the properties recorded. Next, a sample is then typically dissolved in the same fluid medium and the combined mixture is placed in the detection for a reading. Various light wavelengths can then be passed through or scanned through the device. Light is then transmitted or reflected from the molecules in the solution and the results recorded.

More recently, micro-fluidic devices are being used in identifying and characterizing small molecules. These devices avoid the problem of having to use large amounts of sample, transfer sample and take multiple readings to remove baseline contamination readings or low signal to noise. Smaller and smaller samples have been detected, characterized and recaptured using these devices. In certain instances it is possible to quantity the molecules in solution based on some simple laws. For instance, many ultraviolet and visible absorption methods adhere to the Beer Lambert law. The Beer Lambert Law provides that:

$$\epsilon \times bC = A \quad (1)$$

where C is the concentration in moles per liter and is assumed to be constant, A is the minimum detectable absorbance, $\epsilon$ is the molar extinction coefficient and b is the path length (typically 1.0 cm). As one will note from this law that as the concentration C or the path length b are increase the absorbance also increases. In other words the minimum level of detection is increased.

With micro-fluidic devices there are additional parameters that must be considered. For instance, path length (L), the volume (V) as well as well as the cross-sectional area (CSA) of the detection cell are also important in effecting the sensitivity level.

Ideal conditions for improving the signal to noise ratio (sensitivity) require decreasing V, increasing L and decreasing CSA. This provides the optimal conditions for obtaining the best sensitivity. However, most detection cells or devices do not allow for improving each of these parameters. Typically the improvement of one condition causes a negative effect on the other parameters. In the end, this does not improve overall sensitivity levels. For this reason there is a need to improve the overall signal to noise ratios of detection devices and detection cells. In addition, it would be desirable to provide a detection device or cell that minimizes overall sample volume, yet increases L and decreases CSA. To date, few devices and/or detection cells provide the ability to improve each of these parameters to provide improved sensitivity. Most of the present detection devices and detection cells do not provide flexibility for improving these parameters. In addition, it is also desirable to provide a mode of sample transfer and preparation that avoids loss of sample and maximizes the overall sensitivity of the sample detection cell.

These and other problems experience by the prior art have been obviated by the present invention.

SUMMARY OF THE INVENTION

The present invention relates to an apparatus and method for detecting a molecule. The detection cell of the present invention provides a detection cell for receiving and detecting a molecule, comprising a first layer, a detection cell layer contacting the first layer, a micro-fluidic chip contacting the first layer or the detection cell layer and having a fluidic port, and a detection channel defined through the detection cell and being in fluid communication with the fluidic port of the micro-fluidic chip. The detection channel serving as a light path for receiving light for detecting a molecule.

The invention also provides a method of detecting a molecule using a detection cell. The method comprises transmitting light at a molecule in a detection channel, and detecting the light reflected or transmitted from the molecule in the detection channel.

The invention also provides a method for making a detection cell with a micro-fluidic chip, comprising providing a first layer, contacting a detection layer to the first layer, applying a compression force to the detection layer and the first layer to attach the detection layer and first layer and applying a compression force to a micro-fluidic chip and a detection layer and/or first layer to attach the micro-fluidic chip to the first layer and/or detection layer.

BRIEF DESCRIPTION OF THE FIGURES

The invention is described in detail below with reference to the following figures.

DETAILED DESCRIPTION OF THE INVENTION

Figure 1:
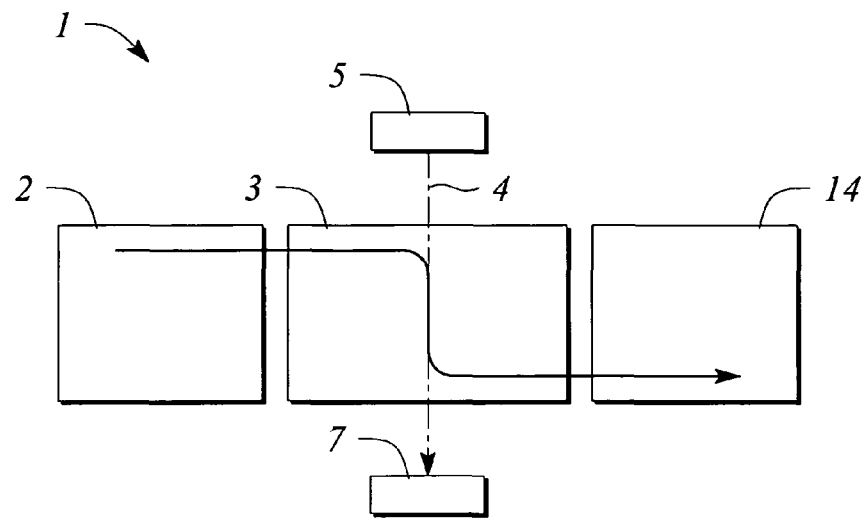
FIG. 1 shows a general perspective view of an embodiment of the present invention.

Before describing the invention in detail, it must be noted that, as used in this specification and the appended claims, the singular forms "a," "an," and "the" include plural referents unless the context clearly dictates otherwise. Thus, for example, reference to "a layer" includes more than one "layer", reference to "a substrate" includes more than one "substrate".

In describing and claiming the present invention, the following terminology will be used in accordance with the definitions set out below.

The term "detection cell" refers to an enclosed or partially enclosed area capable of being used to hold and analyze a sample. Typical detection cells may comprise one or more layers or substrates with one or more detection channels that allow for the transmission of light to the sample.

The term "detection device" refers to a device that may comprise one or more detection cells.

The term "detection layer" refers to a uniform or non-uniform material that may comprise a substrate or a portion of a substrate.

The term "detection channel" refers to an area, chamber, or elongated space or conduit capable of holding and/or allowing for sample movement and/or detection. Detection channel(s) typically are designed within a detection cell or detection device.

The term "fluidic communication" refers to allowing fluid to pass between structures. Samples and/or liquid can also be moved from place to place.

The term "fluidic port" refers to either an inlet port an exit port or both.

The term "layer" refers to a single thickness, coating or stratum spread out or covering a surface.

The term "light" refers to matter that has both wave and particle properties. Typical light used may include and not be limited to ultraviolet light, visible light, infrared, fluorescence light, and bioluminescence light.

The term "light path" refers to the path along which light may travel for detecting a molecule. This may include transmission or reflection.

The term "micro-fluidic" refers to devices that are small in scale.

The term "micro-fluidic chip" refers to a small device capable of separating molecules using small volumes and/or flow rates.

The term "molecule" refers to any material capable of being detected by light transmission, absorbance or reflection.

The term "monolithic" refers to a single structure comprising a homogenous material.

The term "opaque material" refers to a material that prevents or allows only limited light transmission.

The term "substrate" refers to a structure capable of comprising a uniform material or one or more layers of material.

The term "transparent material" refers to a material capable of allowing light to pass through it.

The invention is described herein with reference to the figures. The figures are not to scale, and in particular, certain dimensions may be exaggerated for clarity of presentation.

Referring now to FIGS. 1-5, the optical detection device 1 of the present invention is portrayed. The detection device 1 comprises an input device 2, an optical detection cell 3, a light source 5 and a detector 7. The detector 7 is generally positioned adjacent to the detection cell 3. The input device 2 is positioned adjacent to the detection cell 3. In certain embodiments the input device 2 may be in fluid communication with the detection cell 3.

The input device 2 may comprise any device used for holding or transporting a sample to a micro-fluidic device or similar type device. Input devices are well known in the art. Note in certain embodiments an input device may be omitted. In other embodiments the input device may actual comprise a micro-fluidic device or a portion of a micro-fluidic device.

The light source 5 may comprise any number of light sources known in the art that may be used to identify or characterize a molecule. Light sources are well known in the art that emit and/or reflect light off of various molecules. In particular, light sources may include and not be limited to sources that provide infrared, visible, ultraviolet or other particular wavelengths of light (See FIGS. 2-5).

The detector 7 may comprise any number of common or well known detectors in the art that may be used for detecting light that has been reflected, transmitted, absorbed or scattered from small molecules placed in the detection device 1.

Figure 2:
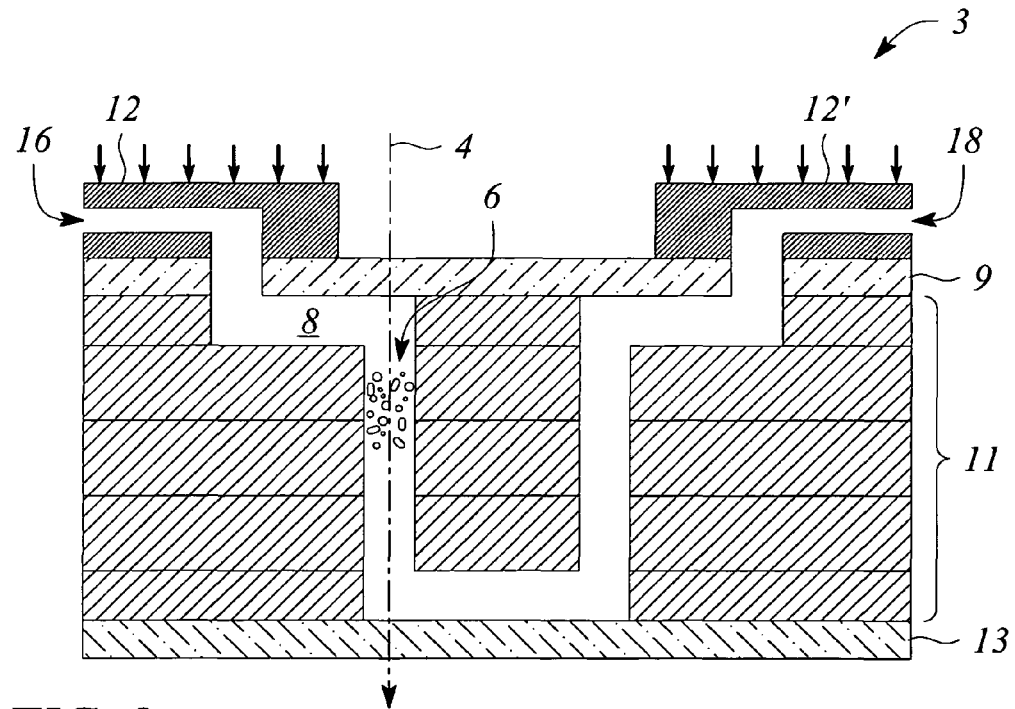
FIG. 2 shows a cross sectional view of a first embodiment of the present invention.

FIG. 2 shows a cross-sectional view of a first embodiment of the invention. The detection cell 3 comprises a first layer 9, a detection layer 11, an optional third layer 13, and one or more micro-fluidic chip(s) 12 and/or 12'. Note that 12 and 12' may in certain instances comprise a micro-fluidic chip. The detection cell 3 provides a detection channel 8 that is designed for receiving a molecule 6. The detection channel 8 defines the light path or a portion of the light path 4 in which the molecule 6 will be identified and/or detected. The length of the light path 4 can be defined or determined by the number of layers or substrates employed in the detection layer 11. The detection layer 11 is important to the invention. The detection layer 11 allows for the flexible construction of the detection cell 3. For instance, 1-15 layers or substrates may be employed to build the detection layer 11. By varying the number of layers or substrates it is possible to change and define the length of the detection channel 8 and/or the light path 4. Being able to alter or define the detection channel 8 and light path 4 is important to the invention. This design provides the ability to increase the overall path length of the light being transmitted through the detection cell 3 to detect the molecule 6. It is particularly important to be able to increase the overall light path length (L) while at the same time reducing the volume (V) of the detection channel 8. In addition, cross sectional area of the channel (CSA) may be reduced. As a result, the overall sensitivity or signal to noise ratio is improved. It should also be noted that molecules 6 may be in static or dynamic movement after they enter the detection channel 8.

The first layer 9 may comprise any number of materials that are transparent to light. For instance, the first layer 9 may comprise a material selected from the group consisting of silicon dioxide, sapphire, pyrex, a transparent polymer, or a quartz material. Other materials known in the art may be employed. Also other materials not described here may be employed. An important functional aspect of the first layer 9 is its ability to allow light or a portion of light to pass through it. Typically the first layer 9 comprises a transparent material. In certain instances, the first layer 9 may comprise a portion of a substrate or the whole substrate. The first layer 9 may comprise other materials or may be monolithic in design.

The detection cell layer 11 contacts the first layer 9. The detection layer 11 may comprise from 1-15 layers or substrates. The thickness of the detection cell layer 11 can, therefore, range from about 0.1 to 10 millimeters depending upon the number of layers and/or substrates employed. Ideally, the detection layer 11 may comprise from 1-5 layers or substrates. Each layer may vary in size or be consistent in width throughout the entire detection cell layer 11. In addition, the detection cell layer 11 may comprise a single material or multiple materials. The composition may be composite, homogenous or heterogenous. The substrate may be monolithic or fragmented into various sections or sub-sections. The detection layer 11 may comprise a portion of a substrate. The detection cell layer 11 may also comprise a transparent or opaque material. The detection cell layer 11 may comprise a material selected from the group consisting of silicon dioxide, sapphire, pyrex, a transparent polymer, a silica wafer or a quartz material.

The third layer 13 is optional to the present invention. In certain instances and embodiments it may contact the detection layer 11. However, this is not a requirement of the invention. It other embodiments the third layer 13 may be eliminated. The third layer 13 may comprise various layers or substrates. The actual width or thickness of the material may be adjusted. The third layer 13 may comprise a number of materials that are transparent to light. For instance, the third layer 13 may comprise a material selected from the group consisting of silicon dioxide, sapphire, pyrex, a transparent polymer, a silica wafer or a quartz material. Other materials known in the art may be employed. Also other materials not described here may be employed. An important functional aspect of the third layer 13 is its ability to allow light or a portion of light to pass through it. Typically the third layer 13 comprises a transparent material. In certain instances, the third layer 13 may comprise a portion of a substrate or the whole substrate. The third layer 13 may comprise other materials or may be monolithic in design.

Figure 4:
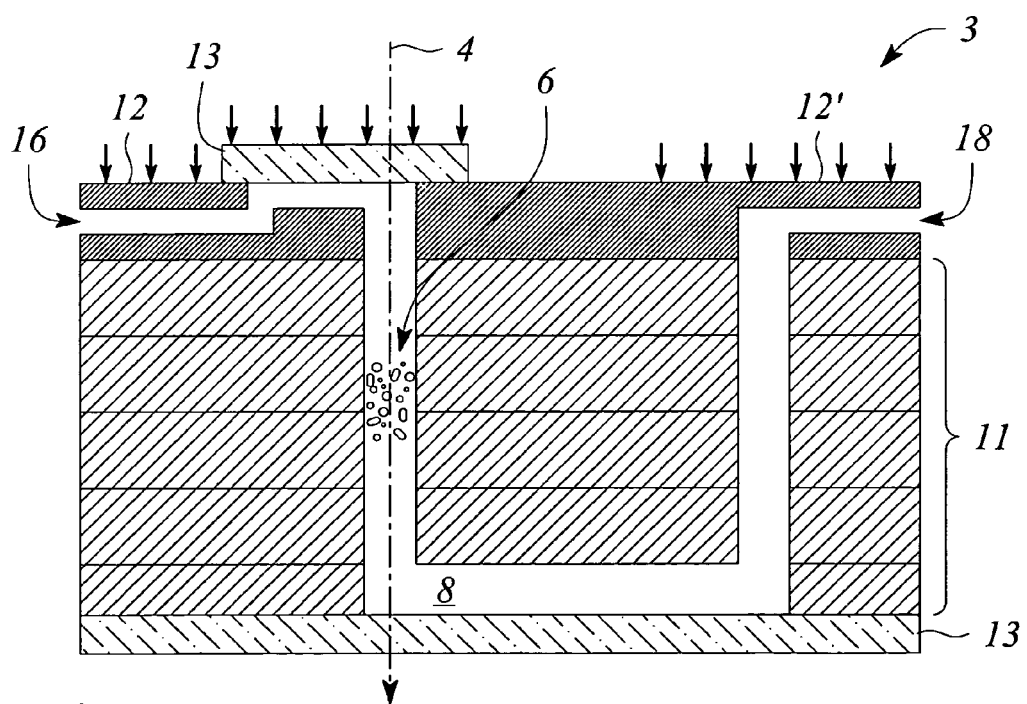
FIG. 4 shows a cross-sectional view of a third embodiment of the present invention.
Figure 5:
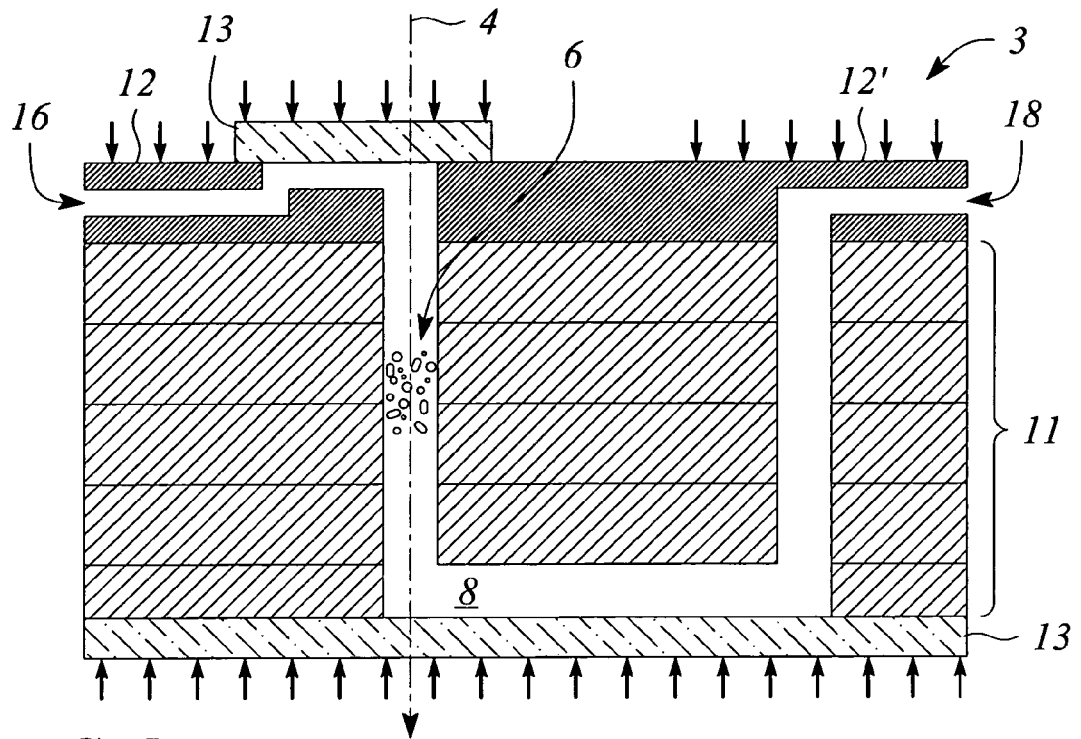
FIG. 5 shows a cross-sectional view of a fourth embodiment of the present invention.

The detection channel 8 is defined by the layers and/or substrates comprising the detection cell layer 11. The detection channel 8 may also be defined by the first layer 9 and the third layer 13. However, this is not a requirement of the invention. In certain embodiments one or more detection channels 8 may be employed with the present invention. The detection channel 8 may have an inlet port 16 and an exit port 18 (See FIGS. 2-5). FIG. 5 shows an embodiment where the light used in the detection is generally reflected down the light path 4 where it exits the detection cell 3. The detector 7 may be placed in any number of locations in or about the detection cell 3. In certain embodiments the detection cell 3 may be designed so that the light is reflected back in the detection channel 8 (back toward the direction from which the light entered the detection channel 8 as opposed to passing through the substrates/layers and exiting the detection cell 3). The internal volume, shape and length of the light path 4 and detection channel 8 can vary. This is an important aspect of the invention. The detection channel 8 may contain a volume of from about 10 to 1000 nanoliters of fluid. Typical flow rates through the channel may vary but can range from around 40-4000 nanoliters/minute.

FIGS. 2-5 show various embodiments of the invention with an altered detection channel 8 and different formats and designs for micro-fluidic chip(s) 12 and/or 12'.

Figure 3:
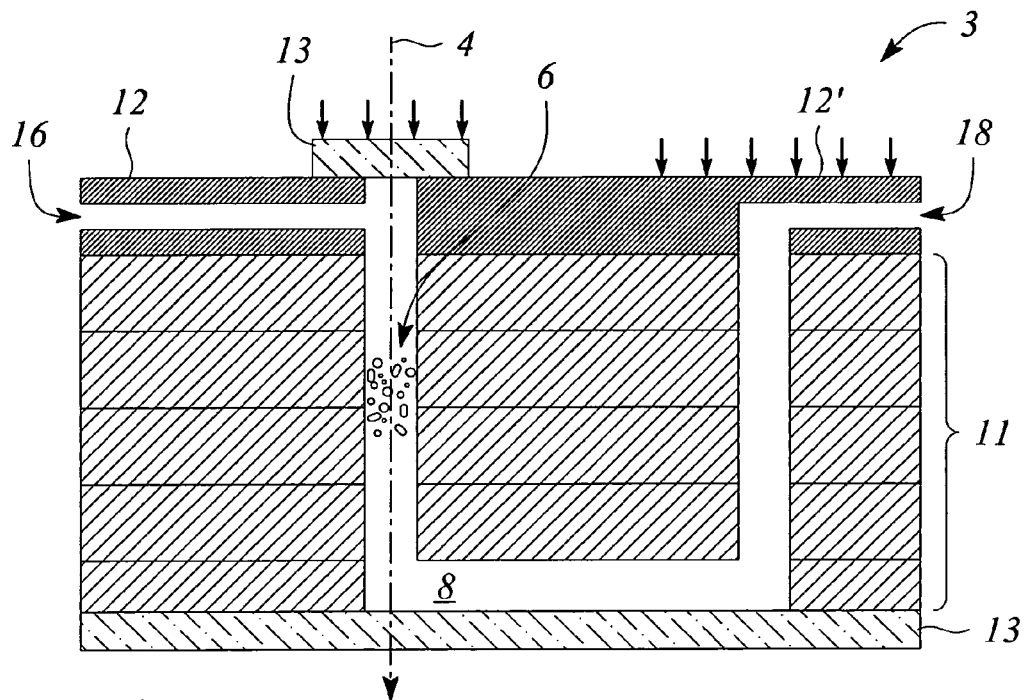
FIG. 3 shows a cross-sectional view of a second embodiment of the present invention.

FIG. 2 shows two micro-fluidic chips 12 and/or 12' contacting the first layer 9. Micro-fluidic chips 12 and 12' may be similar in design or different in design. They are typically well known in the art. Many micro-fluidic chips 12/12' have been designed and are in use for separating/characterizing molecules. The micro-fluidics chips 12 and/or 12' are designed to alter the inlet port 16 and exit port 18 respectively. The micro-fluidics chips 12 and 12' are typically attached to the first layer 9 by application of force to create a compression seal. Each of the FIGS. 2-5 show how the compression forces may be applied to join the micro-fluidic chips 12 and/or 12' (direction of arrows show how and where compression force (s) would ideally be applied) to the surfaces they are contacting (i.e. either first layer 9, detection layer 11, optional layer 13 or combinations of these surfaces). The design of the optical detection cell 3 design described allows for the input, and discharge of the molecules from the same side of the detection cell 3. FIGS. 3-5 show slightly different embodiments of FIG. 2. In each of the disclosed embodiments, sample may be input and discharged to a similar side of the detection cell. This is not a requirement of the invention and the input and exit ports may be positioned in various places about the detection device. Other embodiments and designs may be employed with the present invention. Having described in detail the apparatus of the invention, a brief description of the method is now in order.

Figure 6:
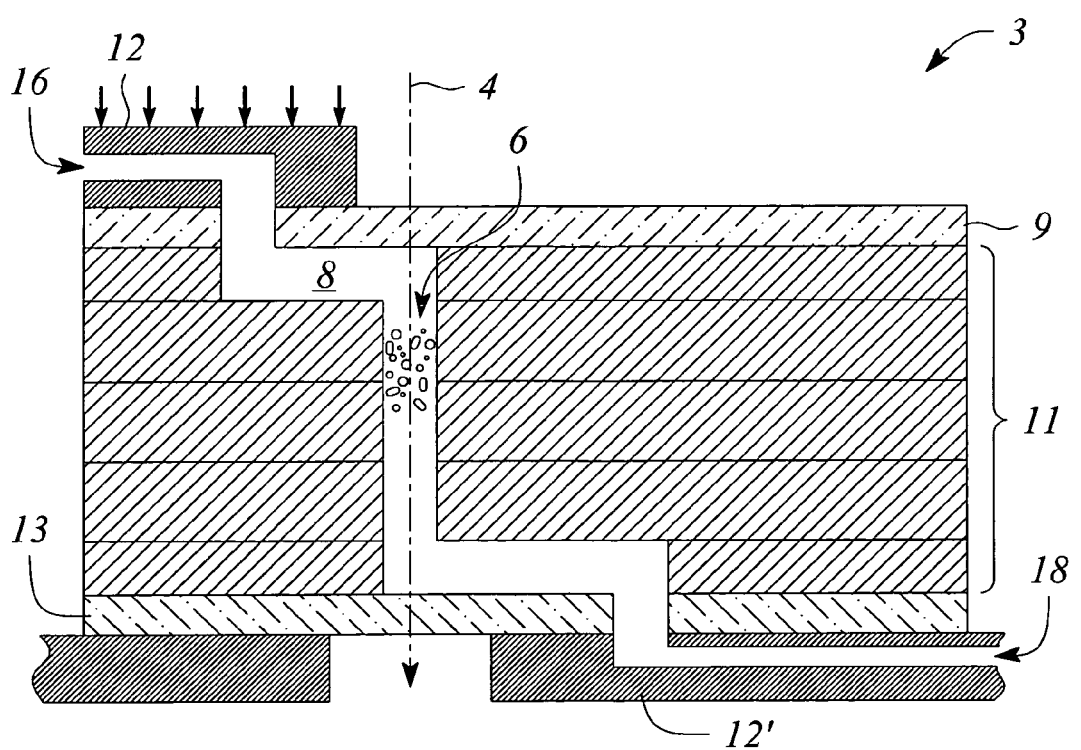
FIG. 6 shows a cross-sectional view of a fifth embodiment of the present invention.

Methods of detecting molecules and making the detection cell 3 will now be described. The method of detecting a molecule 6 is accomplished in a simple manner. Referring now to FIGS. 1-5, the molecule 6 is first input at the inlet port 16 of the optical detection cell 3. The molecule 6 then travels down the detection channel 8. This may be accomplished in a number of ways. Fluids or other mediums may be employed. These fluids, mediums and/or molecules may be moved by pressure and/or electromotive forces. In addition, if a fluid or other medium is employed it may be in a static or dynamic state. After the molecule 6 has entered the detection channel 8 by way of the inlet port 16 it is transported to an area that is accessible to light. First layer 9 comprises a transparent material that allows for light to pass from a light source 5 into the detection channel 8 along the light path 4 (See FIG. 2). Typically, light path 4 is created in a portion of the detection channel 8. The light can then contact or be used to detect a molecule 6 that is positioned in the detection channel 8 along the light path 4. This is generally accomplished by detecting the light that is reflected from the molecule 6 or which passes through the optical detection cell 3. The method of detecting the molecule 6 comprises transmitting light at a molecule 6 in a detection channel 8, and detecting the light transmitted by, emitted by, re-emitted by or reflected from the molecule 6 to the detector 7. The method of making the detection cell 3 with micro-fluidic device 12 and/or 12' comprises a simple process. The method comprises providing a first layer 9, providing a detection cell layer 11 contacting the first layer 9, providing a micro-fluidic chip 12 contacting the detection cell layer 11 and/or the first layer 9 and defining a detection channel 8 through the optical detection cell 3 to serve as a light path 4 for receiving light for detecting a molecule 6. FIGS. 2-6 show how the molecule 6 may be detected in the detection channel 8 using various embodiments of the invention. In each case light is provided by the light source 5 and directed along the light path 4. The light path 4 can range from 0.1 to 10 millimeters in thickness. This may or may not be through one or more layers or substrates. In most embodiments the light passes through detection channel 8 along the light path 4 and exits the optical detection cell at another point. This is not required and as provided in other embodiments, the light from the light source 5 and the signal from the molecule 6 may actually be reflected back toward the light source 5 to exit the same entrance or side it entered the detection channel 8 or light path 4. In other embodiments, the light may be reflected or transmitted out of the optical detection cell 3 in another direction that has not been disclosed or discussed. This is within the scope of the invention. Note that as shown in FIG. 6 the micro-fluidic chip 12 or 12' may actually contact the third layer 13.

We claim:
1. A detection cell, comprising:
a first light-transmissive layer, comprising a solid layer without any cavity therein; and
a detection cell layer having a detection channel defined therein;
wherein at least one of the first light-transmissive layer and the detection cell layer has an exposed surface that is brought into releasable contact with a microfluidic chip to receive at least one molecule therefrom into the detection channel, such that the molecule in the detection channel can be irradiated with light through the first light-transmissive layer and that the resultant light corresponding to the molecule is detectable, the microfluidic chip being releasably sandwiched between the first light-transmissive layer and a first surface of the detection cell layer.
2. A detection cell as recited in claim 1, wherein the detection cell layer has an inlet and an outlet on a same surface of the detection cell layer, and the detection channel connects the inlet to the outlet.

3. A detection cell as recited in claim 1, wherein the detection cell layer comprises a plurality of sub layers.

4. A method of detecting a molecule using the detection cell as recited in claim 1, comprising:
   (a) transmitting light at a molecule in the detection channel; and
   (b) detecting the molecule in the detection channel.

5. An apparatus comprising:
   a microfluidic chip;
   a detection cell that is separate from the microfluidic chip, wherein the detection cell comprises:
   a detection cell layer having a detection channel defined therein;
   a first light-transmissive layer, comprising a solid layer without any cavity therein, the microfluidic chip being releasably sandwiched between the first light-transmissive layer and a first surface of the detection cell layer; and
   a second light-transmissive layer that is fixedly attached to a second surface of the detection cell layer, the second surface being opposite the first surface; and the resultant light is detectable through the second light-transmissive layer, wherein during use, the detection cell is brought into releasable contact with the microfluidic chip to receive at least one molecule therefrom into the detection channel, such that the molecule in the detection channel can be irradiated with light through the first light-transmissive layer and that the resultant light corresponding to the molecule is detectable.

6. An apparatus according to claim 5, wherein:
the first light transmissive layer is fixedly attached to the detection cell layer, and the first light-transmissive layer is brought into releasable contact with the microfluidic chip during use, the first light transmissive layer having an opening through which the at least one molecule is received from the microfluidic chip into the detection channel of the detection cell layer.

7. An apparatus according to claim 6, wherein:
the first light-transmissive layer is fixedly attached to a first surface of the detection cell layer,
the detection cell further comprises a second light-transmissive layer that is fixedly attached to a second surface of the detection cell layer, the second surface being opposite the first surface; and
the resultant light is detectable through the second light-transmissive layer.

8. An apparatus according to claim 5, wherein:
the detection cell layer has an inlet and an outlet on a same surface of the detection cell layer, and the detection channel connects the inlet to the outlet.

9. An apparatus according to claim 5, wherein the detection cell layer comprises a plurality of sub layers.

* * * * *

UNITED STATES PATENT AND TRADEMARK OFFICE
CERTIFICATE OF CORRECTION

PATENT NO. : 8,647,590 B2  
APPLICATION NO. : 11/384149  
DATED : February 11, 2014  
INVENTOR(S) : Reid A. Brennen et al.

Page 1 of 1

It is certified that error appears in the above-identified patent and that said Letters Patent is hereby corrected as shown below:

On the title page, item (56), under "Other Publications", in column 2, line 5, delete "2013" and insert -- 2012 --, therefor.

In the Claims:

In column 8, line 4, in claim 6, delete "light transmissive" and insert -- light-transmissive --, therefor.

In column 8, line 7, in claim 6, delete "light transmissive" and insert -- light-transmissive --, therefor.

Signed and Sealed this
Twentieth Day of May, 2014

Michelle K. Lee
*Deputy Director of the United States Patent and Trademark Office*